(12) United States Patent
Carroll et al.

(10) Patent No.: US 10,463,807 B2
(45) Date of Patent: Nov. 5, 2019

(54) MEDICAL INJECTION DEVICE HAVING A TELESCOPICALLY MOVABLE SHIELD

(71) Applicant: Novo Nordisk A/S, Bagsvaerd (DK)

(72) Inventors: Ronan Carroll, Tisvildeleje (DK); Morten Revsgaard Frederiksen, Copenhagen (DK); Lars Eilertsen, Fredensborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 241 days.

(21) Appl. No.: 15/562,959

(22) PCT Filed: Apr. 1, 2016

(86) PCT No.: PCT/EP2016/057233
§ 371 (c)(1),
(2) Date: Sep. 29, 2017

(87) PCT Pub. No.: WO2016/162284
PCT Pub. Date: Oct. 13, 2016

(65) Prior Publication Data
US 2018/0110935 A1  Apr. 26, 2018

(30) Foreign Application Priority Data

Apr. 10, 2015 (EP) .................................... 15163099

(51) Int. Cl.
*A61M 5/32* (2006.01)
*A61M 5/00* (2006.01)
*A61M 5/24* (2006.01)

(52) U.S. Cl.
CPC .......... *A61M 5/3245* (2013.01); *A61M 5/001* (2013.01); *A61M 5/24* (2013.01);
(Continued)

(58) Field of Classification Search
CPC ...... A61M 5/001; A61M 5/24; A61M 5/3202; A61M 5/3245; A61M 2209/10
See application file for complete search history.

(56) References Cited

U.S. PATENT DOCUMENTS 3,354,881 A  11/1967 Bloch
4,416,663 A  11/1983 Hall
(Continued)

FOREIGN PATENT DOCUMENTS

WO  2011048223 A1  4/2011
WO  2014029018 A1  2/2014
(Continued)

*Primary Examiner* — Laura A Bouchelle
(74) *Attorney, Agent, or Firm* — Wesley Nicolas (57) ABSTRACT

The invention relates to a pre-filled injection device for apportioning a plurality of set doses of a liquid drug comprising. The housing of the injection device supports a non-replaceable cartridge containing the liquid drug. The cartridge is e.g. secured in a cartridge-holder being a part of the housing. A needle assembly comprising a needle cannula secured in a hub is slidable mounted to slide into contact with the cartridge. The tip of the needle cannula is covered by a telescopically movable shield movable from an extended position to a retracted position. The telescopically movable shield supports a cleaning chamber containing a cleaning solvent for cleaning at least the distal tip of the needle cannula between subsequent injections. The distal end of the housing supports a removable protective cap and the telescopically movable shield is guided relatively to the housing and coupled to the protective cap to follow movement of the protective cap.

11 Claims, 6 Drawing Sheets

(52) U.S. Cl.
CPC ........ *A61M 5/2429* (2013.01); *A61M 5/3202* (2013.01); *A61M 5/3243* (2013.01); *A61M 5/3216* (2013.01); *A61M 5/3257* (2013.01); *A61M 2209/10* (2013.01)

(56) References Cited

U.S. PATENT DOCUMENTS

| | | |
|---|---|---|
| 4,507,118 A | 3/1985 | Dent |
| 4,666,436 A | 5/1987 | McDonald et al. |
| 7,374,558 B2 | 5/2008 | Kirchhofer |
| 2012/0316508 A1 | 12/2012 | Kirchhofer |
| 2014/0228769 A1 | 8/2014 | Karlsson et al. |

FOREIGN PATENT DOCUMENTS

| | | |
|---|---|---|
| WO | 2014064100 A1 | 5/2014 |
| WO | 2015062845 A1 | 5/2015 |
| WO | 2015173151 A1 | 11/2015 |

MEDICAL INJECTION DEVICE HAVING A TELESCOPICALLY MOVABLE SHIELD

CROSS-REFERENCE TO RELATED APPLICATIONS

This application is a 35 U.S.C. § 371 National Stage application of International Application PCT/EP2016/057233 (published as WO 2016/162284), filed Apr. 1, 2016, which claims priority to European Patent Application 15163099.3, filed Apr. 10, 2015; the contents of which are incorporated herein by reference.

THE TECHNICAL FIELD OF THE INVENTION

The invention relates to a medical injection device for injecting a liquid drug and especially to a pre-filled injection device for apportioning a plurality of individual settable doses. The invention especially relates to such pre-filled injection device wherein the same needle cannula is used for a multiple number of injections and wherein at least the distal tip of the needle cannula is cleaned between every injection.

DESCRIPTION OF RELATED ART

Injection devices wherein the tip of the needle cannula is maintained in a cleaning solvent between subsequent injections are disclosed in U.S. Pat. Nos. 3,354,881, 4,416,663, 4,507,118 and in U.S. Pat. No. 4,666,436. As can be seen from these prior art injection devices, the cleaning chamber is usually carried distally on a retractable shield covering the tip of the needle cannula between subsequent injections.

Further WO2014/064100 discloses a pre-filled disposable injection device which has a telescopically movable shield covering the tip of the needle cannula between subsequent injections. This telescopically movable shield is urged into a distal covering position by a compression spring. Further, in one embodiment, the shield is provided with a hollow chamber containing a liquid solvent such as a chemical disinfectant or biocide which cleans the tip of the needle cannula between subsequent injections. When not in use the distal end of the pen-shaped injection device is preferably concealed by a removable protective cap. This removable cap is in one example internally provided with a sponge which can be pressed against the distal end of the pen-shaped injection device in order to clean the outside surface of the distal end.

Examples on such cleaning solvents are provided in WO 2014/029018. However, as disclosed in WO 2015/062845 it is sometime preferred to use the same preservative as contained in the drug as the cleaning solvent to avoid that the liquid drug is being contaminated by a different cleaning solvent. This can be done by filling the cleaning chamber with the same liquid drug as present in the injection device. The injection device can henceforth be delivered to the user with the same liquid drug filled into both the cartridge and into the cleaning chamber. Alternatively, the user can fill the cleaning chamber with liquid drug directly from the cartridge embedded in the pre-filled injection device by performing a specific initiation procedure which automatically transfers a predetermined volume of the liquid drug from the cartridge and into the cleaning chamber.

However, when transferring the predetermined volume of liquid drug from the cartridge to the cleaning chamber various tolerances apply with the result that the volume transferred can be larger than the volume of the cleaning chamber whereby an overpressure can be introduced into the closed liquid system. Further, when storing the injection device changing temperature conditions can also lead to an overpressure being introduced in the liquid system.

Such overpressure in the liquid system is however unwanted since it can lead to an unwanted overdosing.

DESCRIPTION OF THE INVENTION

It is thus an object of the present invention to provide a pre-filled injection device having the possibility of equalizing the pressure in the liquid system preferably by venting the liquid system after a quantum of the liquid drug has been transferred to the cleaning chamber.

By such venting procedure, the pressure inside the cartridge and inside the liquid system is aligned with the outside pressure such that the doses set by the user equals the doses actually expelled.

Accordingly, in one aspect of the present invention, the pre-filled injection device comprises:

A housing which extends in a longitudinal direction, the housing preferably comprises a cartridge-holder as a part of the housing. The cartridge-holder holds the cartridge containing the liquid drug.

A removable protective cap mountable onto the housing and covering at least the distal end of the housing when mounted and which protective cap can be manipulated and removed by the user.

A non-replaceable cartridge permanently embedded in the housing of the pre-filled injection device which housing also comprises the cartridge-holder. The cartridge is secured to the housing such that it can only be removed by destroying the housing surrounding and embedding the cartridge. The cartridge has a hollow interior containing the liquid drug to be injected.

A needle assembly which comprises a needle cannula secured in a hub preferably by gluing or welding. The needle cannula has a distal end with a distal tip and a proximal end and a lumen connecting the two ends. The proximal end of the needle cannula is insertable into the cartridge of the injection device while the distal tip penetrates the skin of a user during injection. The proximal end is either positioned inside the cartridge when the injection device is delivered to the user, or the proximal end is inserted into the cartridge by the user through a defined initiation procedure.

A telescopically movable shield movable from an extended position covering at least the distal tip of the needle cannula to a retracted position. The telescopically movable shield is preferably moved to the retracted position by being pressed against the skin of a user during injection. The telescopically movable shield further supports a cleaning chamber containing an amount of the same liquid drug as contained in the cartridge for cleaning at least the distal tip of the needle cannula between subsequent injections.

By the term "pre-filled injection device" is meant that the cartridge is located internally in the housing which is irreversible sealed. The cartridge is thus permanently connected to the housing. As a result of being "pre-filled", the cartridge which is filled with a predetermined quantum of liquid drug is non-replaceable embedded in the housing of the injection device which must therefore be discarded when the liquid drug contained in the embedded cartridge has been used. Often the housing also comprises a cartridge-holder as a part of the housing.

The liquid drug contained in the cartridge and transferred to the cleaning chamber to operate as a cleaning solvent contains one or more preservatives which are the active substance doing the actual cleaning of the distal tip of the needle cannula between injections.

The telescopically movable shield carrying the cleaning chamber is moved axially in relation to the housing during injection such that after the cleaning chamber has been filled with a quantum of liquid drug from the cartridge, the distal tip of the needle cannula is maintained submerged in the liquid drug in the cleaning chamber between injections. However, in order to vent the liquid system, the telescopically movable shield and thus the cleaning chamber is moved to a position in which the distal tip of the needle cannula protrudes in front of the cleaning chamber. In this venting position where the distal tip of the needle cannula is outside the cleaning chamber and not inserted into the skin of a user, the inside pressure is equalized with the pressure of the surroundings.

The backwards movement of the telescopically movable shield and the cleaning chamber is preferably done by the user manipulating the removable protective cap covering the distal end of the housing of the pen-shaped injection device. In a preferred embodiment the removable protecting cap engages the telescopically movable shield such that rotation of the protective cap relatively to the housing is transformed to a simultaneously rotation of the telescopically movable shield.

The telescopically movable shield is thus preferably arranged such that rotation of the telescopically movable shield also moves the shield in the proximal direction to a position in which the distal tip of the needle cannula is located in front of the cleaning chamber carried by the telescopically movable shield. This axial movement of the telescopically movable shield introduced by rotation of the telescopically movable shield can be accomplished in various different ways e.g. by providing of threaded interface moving the telescopically movable shield in the proximal direction whenever rotated. Using a threaded connection results in that the telescopically movable shield defines a helically movement when rotated.

It is thus to be understood that movements of the shield described as axially or telescopically can be both purely axial movements or it can be helical movements. Purely axial is where the parts slides relatively to each other without any rotation whereas helically movement is a movement wherein the parts simultaneously move both axially and rotational as in a threaded connection.

By having the protective cap rotationally engaging the rotatable and telescopically movable shield the user needs not physically touch the telescopically movable shield which significantly lowers the risk of needle injuries as the users hand and fingers stays protected by the protective cap.

In one embodiment, the protective cap is internally provide with means for engaging the telescopically and rotatable shield. These means can be formed in many different ways but are in one example formed as one or more inwardly pointing ribs or protrusions engaging similar ribs or protrusions provided on the outer surface of the telescopically movable shield such that rotation of the protective cap is transferred to a similar rotation of the telescopically movable shield via these ribs or protrusions.

In another example, the means are provided internally in the protective cap as gripping means engaging a longitudinal track provided in the telescopically movable shield such that the telescopically movable shield rotates whenever the gripping means are rotated, which is whenever the protective cap is rotated. By gripping means is meant any means which can grip into a track. All though an even number of gripping means and tracks is usually provided in order to equally distribute the rotational forces used any random number can be provided.

The gripping means are preferably provided with shoulders which are able to axially transferring a force to the telescopically movable shield such that when a user pushes the protective cap proximally, the telescopically movable shield follows this movement. This axial movement can e.g. be transferred to the needle assembly such that the proximal end of the needle cannula is inserted into the cartridge by this movement.

In one embodiment, the telescopically movable shield is provided with a guiding track for thereby controlling the movement of the telescopically movable shield as it is rotated by the protective cap. The guiding track surrounds an outwardly pointing protrusion provided on the injection device which thus guides the telescopically movable shield such that the shape of the guiding track is decisive for the resulting movement of the telescopically movable shield.

The guiding track is preferably helically and can have any desired length. It can e.g. be shorter than 360 degrees such that the full axial movement is obtained by less than a full revolution, or it can be an actual threaded connection requiring several full rotations.

The protrusion can be provided on any part of the injection device and in any position but is preferably positional locked to the housing e.g. by being provided directly on the housing or on a part which is secured to the housing. Further, in any embodiment, more than one protrusion and more than one guiding track can be provided.

In an alternative embodiment, the outwardly pointing protrusion can be provided as an internal protrusion on the telescopically movable shield and the guiding track can be provided in the housing or in a part coupled to the housing.

The guiding track is preferably divided into different track parts and preferably into a helical track part supplemented by a first axial track part and a second axial track part which preferably is connected by the helical track part. When the outwardly pointing protrusion is disposed in the helical track and the telescopically movable shield is rotated via the protective cap, the resulting movement of the telescopically movable shield is a helical movement.

When the outwardly pointing protrusion is located in either of the two axial track parts connected to the helical tracks, the telescopically movable shield is bound to travel in the longitudinal direction. Axial movement from the retracted position to the extended position is preferably operated by a resilient element such as a compression spring urging the telescopically movable shield in the distal direction.

The guiding of the telescopically movable shield in relation to the protrusion could also be envisaged without using the protective cap to move the telescopically movable shield. In such case the telescopically movable shield can be directly manipulated by the user, however, as previously mentioned this would expose the user to the risk of needle stick injuries.

As an alternative to the protrusion, the telescopically movable shield can be guided in a threaded connection with the housing such that continued rotation of the protective cap engaging the telescopically movable shield rotates the telescopically movable shield in the proximal direction. However, it will in such embodiment be necessary to guide the telescopically movable shield into an axial track in order to have the telescopically movable shield move distally to the ready-to-use situation.

In one example the slidable mounted needle assembly is carrying the outwardly pointing protrusion such that axial movement of the telescopically movable shield can be transferred to an axial movement of the needle assembly e.g. via the protrusion. This axial movement could potentially be used to penetrate the proximal end of the needle cannula through the septum of the cartridge in order to create a liquid communication.

The needle assembly is preferably axially locked to the housing such that the needle assembly is restricted to purely axial movement. In this manner the outwardly pointing protrusion when positioned on the needle assembly is also rotational locked in relation to the housing.

Once the needle assembly has been axially moved to its engaged position it should be axially locked in this position such that when the protective cap and the telescopically movable shield is rotated the protrusion is permanently maintained in this locked position should the protrusion be provided on the needle hub.

Definitions

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

The term "Needle Cannula" is used to describe the actual conduit performing the penetration of the skin during injection. A needle cannula is usually made from a metallic material such as e.g. stainless steel and connected to a hub to form a complete injection needle also often referred to as a "needle assembly". A needle cannula could however also be made from a polymeric material or a glass material. The hub also carries the connecting means for connecting the needle assembly to an injection apparatus and is usually moulded from a suitable thermoplastic material.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Cartridge" is the term used to describe the container actually containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. Such septum is usually self-sealing which means that the opening created during penetration seals automatically by the inherent resiliency once the needle cannula is removed from the septum. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Since a cartridge usually has a narrower distal neck portion into which the plunger cannot be moved not all of the liquid drug contained inside the cartridge can actually be expelled. The term "initial quantum" or "substantially used" therefore refers to the injectable content contained in the cartridge and thus not necessarily to the entire content.

By the term "Pre-filled" injection device is meant an injection device in which the cartridge containing the liquid drug is permanently embedded in the injection device such that it cannot be removed without permanent destruction of the injection device. Once the pre-filled amount of liquid drug in the cartridge is used, the user normally discards the entire injection device. This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using pre-filled injection devices an average user might require as many as 50 to 100 injection devices per year whereas when using durable injection devices one single injection device could last for several years, however, the average user would require 50 to 100 new cartridges per year.

"Scale drum" is meant to be a cylinder shaped element carrying indicia indicating the size of the selected dose to the user of the injection pen. The cylinder shaped element making up the scale drum can be either solid or hollow. "Indicia" is meant to incorporate any kind of printing or otherwise provided symbols e.g. engraved or adhered symbols. These symbols are preferably, but not exclusively, Arabian numbers from "0" to "9". In a traditional injection pen configuration the indicia is viewable through a window provided in the housing.

Using the term "Automatic" in conjunction with injection device means that, the injection device is able to perform the injection without the user of the injection device delivering the force needed to expel the drug during dosing. The force is typically delivered—automatically—by an electric motor or by a spring drive. The spring for the spring drive is usually strained by the user during dose setting, however, such springs are usually prestrained in order to avoid problems of delivering very small doses. Alternatively, the spring can be fully preloaded by the manufacturer with a preload sufficient to empty the entire drug cartridge though a number of doses. Typically, the user activates a latch mechanism e.g. in the form of a button on, e.g. on the proximal end, of the injection device to release—fully or partially—the force accumulated in the spring when carrying out the injection.

The term "Permanently connected" as used in this description is intended to mean that the parts, which in this application is embodied as a housing and a cartridge, requires the use of tools in order to be separated and should the parts be separated it would permanently damage at least one of the parts thus rendering the injection device as such useless.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device which usually carries the injection needle whereas the term "proximal end" is meant to refer to the opposite end pointing away from the injection needle and usually carrying the dose dial button.

Figure 12:
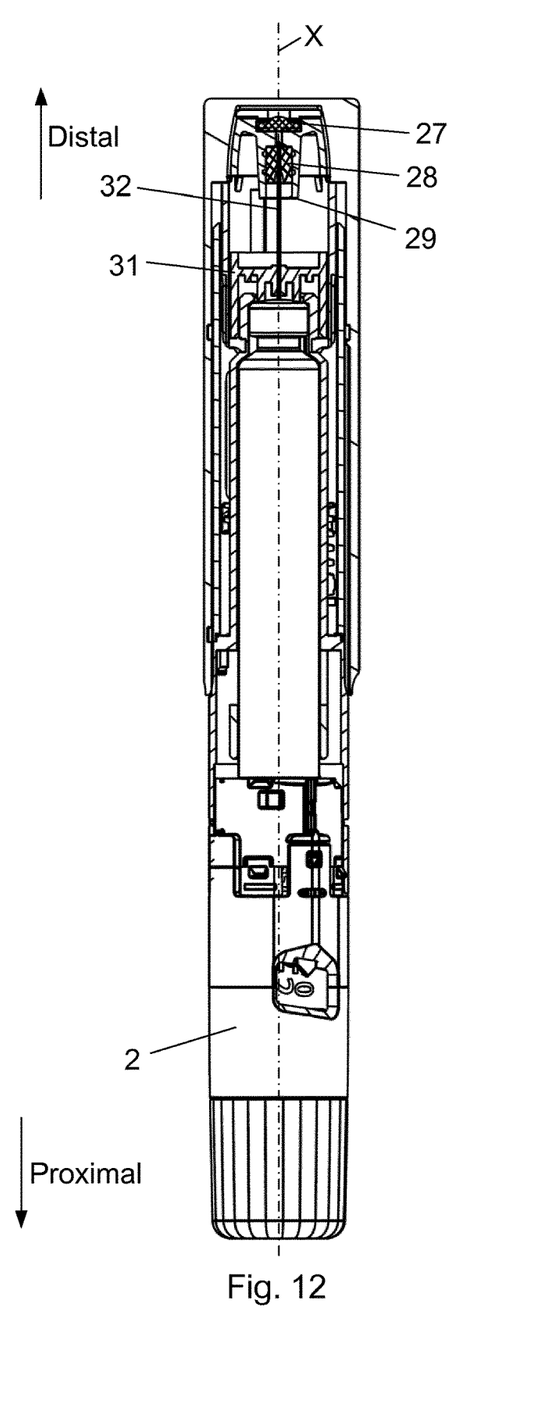
FIG. 12 show a cross sectional view of the injection device with the protective cap moved proximally as disclosed in FIG. 2 and FIG. 7.

Further, as indicated in FIG. 12, the axis "X" is the longitudinal centre axis of the injection device and thus defines the axial direction of the injection device herein disclosed as being pen-shaped.

Figure 11:
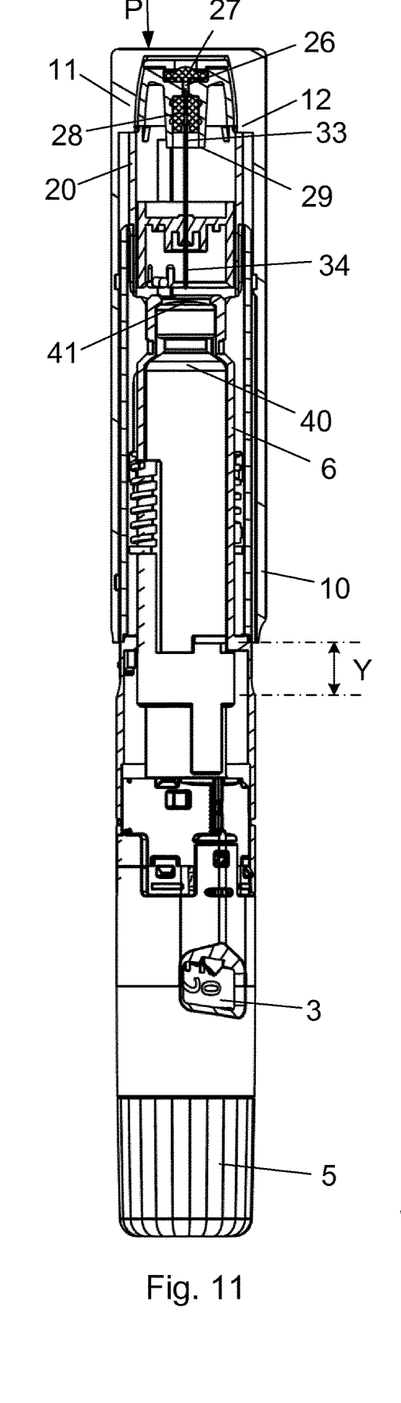
FIG. 11 show a cross sectional view of the injection device in the initial position as disclosed in FIG. 1 and in FIG. 6.

Distal and proximal is further indicated in FIG. 11 which also shows the axial axis "X" of the injection device 1.

FIGS. 1 to 4 discloses the injection device 1 according to a first embodiment.

Proximally the injection device 1 is provided with a dose setting button 5 that the user can rotate in order to set the dose. The dose setting button 5 is axially secured to the housing 2 such that the dose setting button 5 does not translate axially when rotated. The dose set by this rotation is shown by indicia on a scale drum appearing in a dose window 3 in the housing 2.

The distal end of the injection device 1 is in FIGS. 1 to 3 covered by a removable protective cap 10 which can be manipulated by the user as will be explained.

Figure 4:
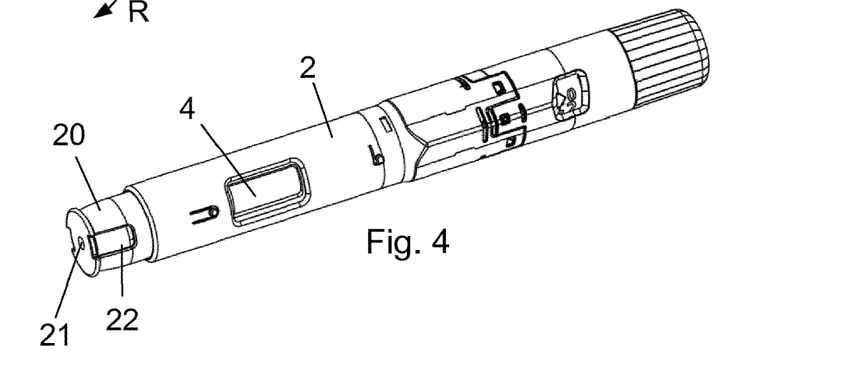
FIG. 4 show a perspective view of the injection device with the protective cap removed.

FIG. 4 depicts the injection device 1 with the protective cap 10 removed. Distally a telescopically movable shield 20 covers the needle cannula 32 (shown in FIG. 5). Further in FIG. 4, the protective cap 10, when mounted, covers a window 4 in the housing 2, through which window 4, the user is able to visually inspect the drug contained in the cartridge 40 embedded in injection device 1.

The telescopically movable shield 20 is able to move in a proximal direction and is urged distally by a non-shown resilient element such as a spring. The distal end of the telescopically movable shield 20 has an opening 21 through which the needle cannula 32 can protrude and is further provided with longitudinal tracks 22 which are engaged by gripping means 11 provided internally in the protective cap 10 as best seen in FIG. 11.

Figure 5:
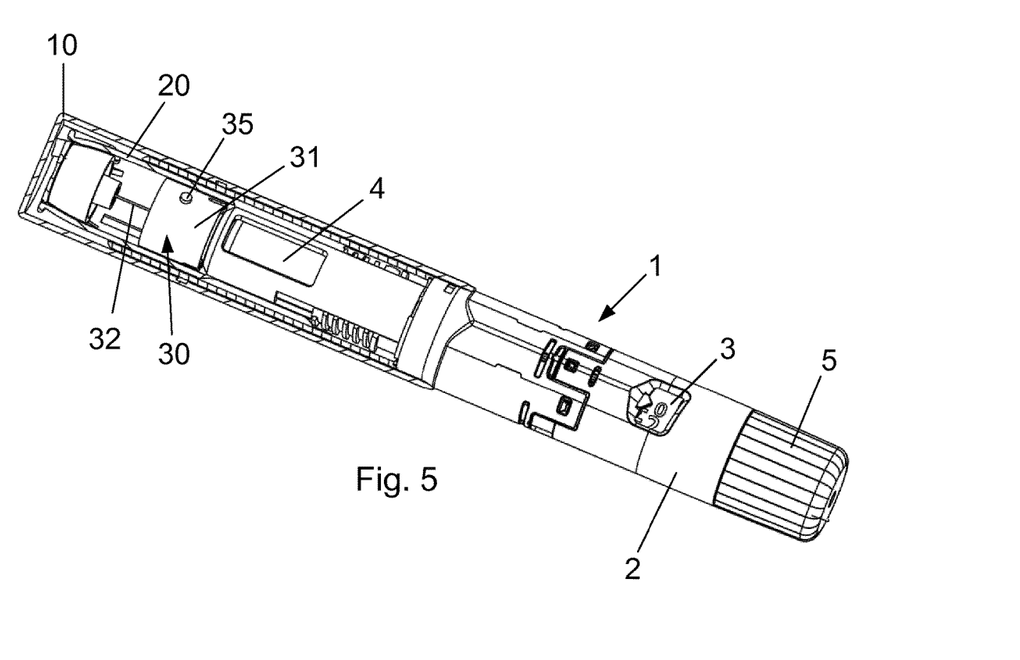
FIG. 5 show a cross sectional view of the injection device according to the invention.
Figure 6:
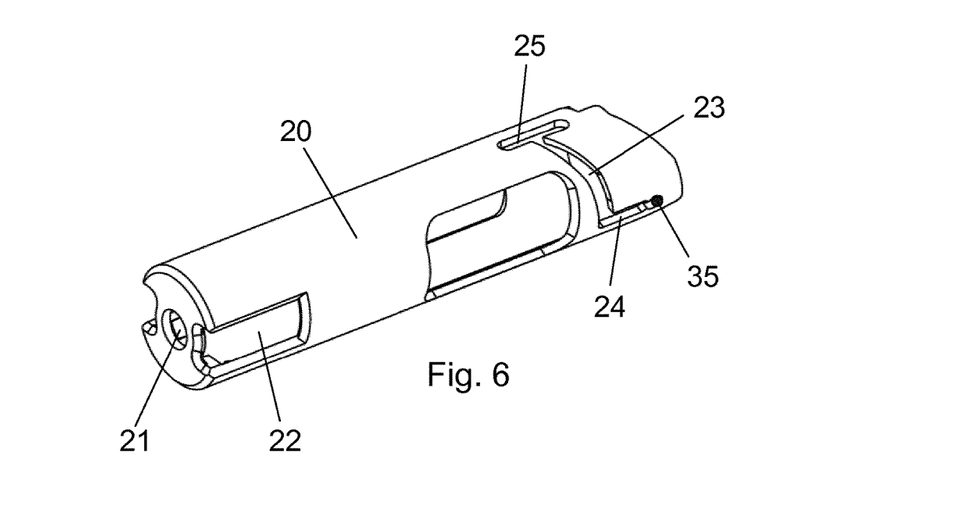
FIGS. 6 to 10 show perspective views of the telescopically movable shield.

The injection device 1 is further disclosed in FIG. 5. The shield 20 covers the needle assembly 30 which comprises a hub 31 and a needle cannula 32 connected to the hub 31. The hub 31 is further provided with an outwardly pointing protrusion 35 and the hub 31 is able to slide axially in relation to the housing 2 but is rotational secured to the housing 2 such that the hub 31 and thus the needle assembly 30 can only slide axially without rotation.

The telescopically movable shield 20 is as disclosed in FIGS. 6 to 10 besides the opening 21 and the longitudinal tracks 22 further provided with a guiding track 23, 24, 25 which guides the shield 20 in relation to the outwardly pointing protrusion 35. This guiding track 23, 24, 25 has a helical track part 23 helically connecting a first axial track part 24 with a second axial track part 25.

In the above embodiment the protrusion 35 is positioned on the needle hub 31 as depicted in FIG. 5 but the protrusion 35 could in a different embodiment be disposed anywhere on the outer surface of the part of the housing 2 supporting the shield 20. The guiding track 23, 24, 25 could also be provided in a different position than disclosed in the figures as long as the protrusion 35 slides in the guiding track 23, 24, 25.

The injection device 1 is disclosed in further details in the FIGS. 11 to 16 and comprises;

The housing 2 which proximally holds the dose setting button 5. Further, the housing 2 secures the cartridge 40 which hold the liquid drug to be injected. A cartridge-holder 6 can be present as a part of the housing 2. The cartridge-holder 6 can either be moulded as an integral part of the housing 2 or it can be a separate part permanently connected to the housing 2. The cartridge 40 is distally provided with a septum 41 to be pierced by the needle cannula 32 as will be explained. Proximally the cartridge 40 is provided with the usual plunger which is moved forward by a drive mechanism including a piston rod.

The protective cap 10 provided with internal gripping means 11 for interacting with the telescopically movable shield 20. The gripping means 11 is formed to rotational interact with the telescopically movable shield 20 via the longitudinal tracks 22 provided in the telescopically movable shield 20 and is further shaped with shoulders 12 to engage with the telescopically movable shield 20 in the longitudinal direction. Further, the proximal cap 10 is slidable in an axial direction in relation to the housing 2. As seen in e.g. FIG. 11, the shoulders 12 abut the proximal end of the longitudinal tracks 22.

The telescopically movable shield 20 which distally carries, as e.g. seen in FIGS. 11 to 16, a cleaning chamber 26 which is encompassed between a distal septum 27 and a proximal piston 28.

The needle assembly 30 which comprises the hub 31 with the needle cannula 32 attached thereto. The needle cannula 32 has a distal part 33 protruding in a distal direction from the hub 31 and a proximal part 34 protruding in the proximal direction from the hub 31. The distal part has a sharp tip 36 (FIG. 14) for penetrating the skin of the user during injection.

Figure 1:
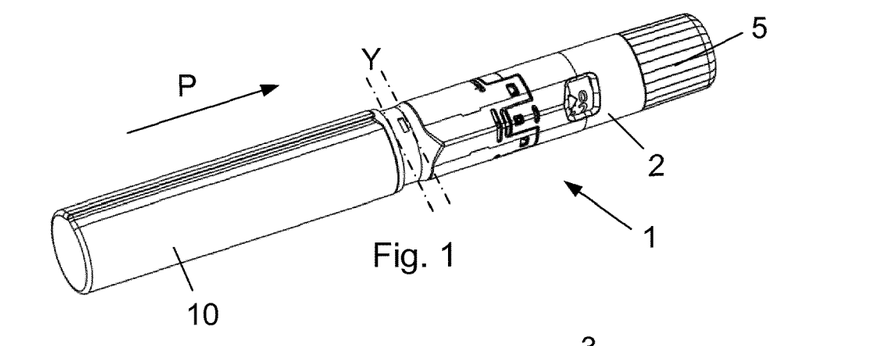
FIG. 1 show a perspective view of the injection device in the initial state.

When the injection device 1 is delivered to the user, the protective cap 10 is not fully moved to its proximal position as disclosed in FIG. 1 and FIG. 11. In this initial position the outwardly protrusion 35 provided on the hub (31) or on a part of housing 2 (e.g. the on the cartridge-holder 6) is held in the proximal end of the first axial track 24 as disclosed in FIG. 6.

In order to start using the injection device 1, the user applies a pressure "P" to the protective cap 10 thus pushing the protective cap 10 in the proximal direction a distance "Y" as indicated in FIG. 1 and FIG. 11. This axial movement is transferred to a proximal movement of the telescopically movable shield 20 via the shoulders 12 of the gripping means 11 such that the telescopically movable shield 20 moves proximally together with the protective cap 10.

Figures 7, 8:
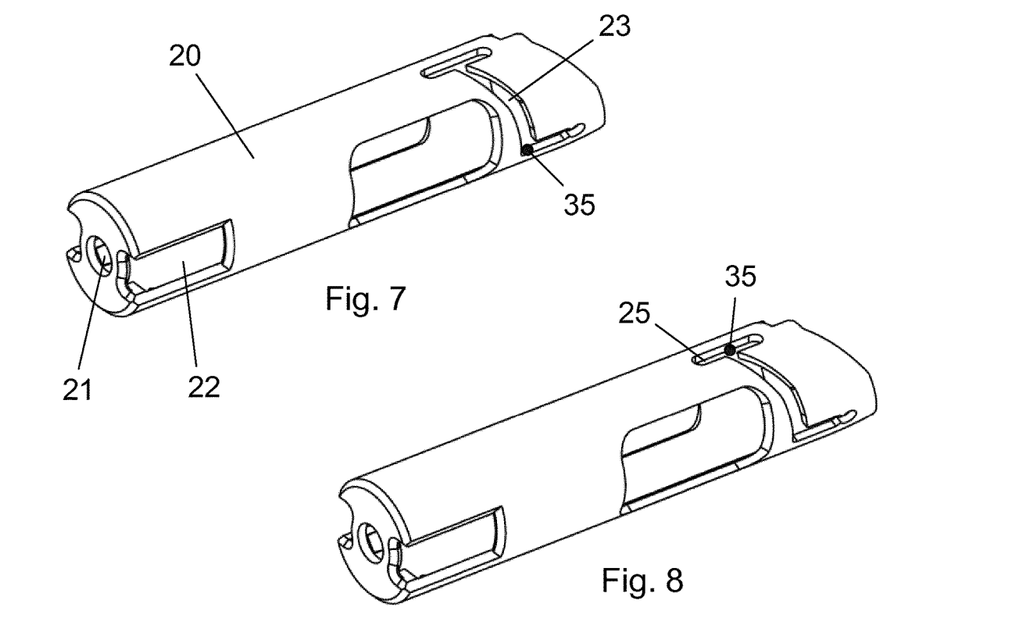

As the telescopically movable shield 20 move proximally the outwardly protrusion 35 move to the distal end of the first axial track 24 as disclosed in FIG. 7. The axial movement of the shield 20 also moves the needle assembly 30 in the proximal direction. As a result the needle assembly 30 and thus the needle cannula 32 are moved proximally whereby the proximal part 34 of the needle cannula 32 penetrates through the distal septum 41 of the cartridge 40 as disclosed in FIG. 12.

Figures 2, 3:
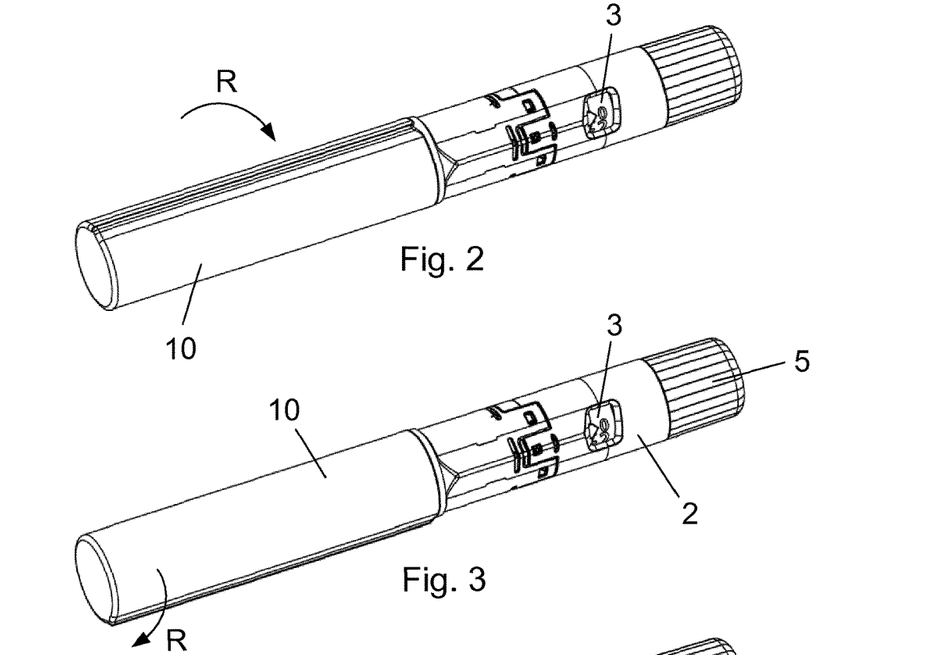
FIG. 2 show a perspective view while rotating the protective cap.
FIG. 3 show a perspective view while continuing rotation of the protective cap.

In this situation disclosed in FIG. 2 and FIG. 12 the interior of the cartridge 40 is in liquid communication with the cleaning chamber 26 which can then be filled with liquid drug from the cartridge 40.

The filling can be done either manually by the user expelling liquid drug directly into the cleaning chamber 26 or it can be done automatically by providing the interior of the cartridge 40 with an overpressure such that liquid drug will start to flow once the distal end 34 of the needle cannula 32 penetrates through the septum 41.

The overpressure can thus either be existing inside the cartridge 40 when the injection device 1 is delivered to user or it can be introduced by the user e.g. by moving the cartridge 40 and the drive mechanism relatively to the each other in an axial direction when initiating the injection device 1.

Figure 13:
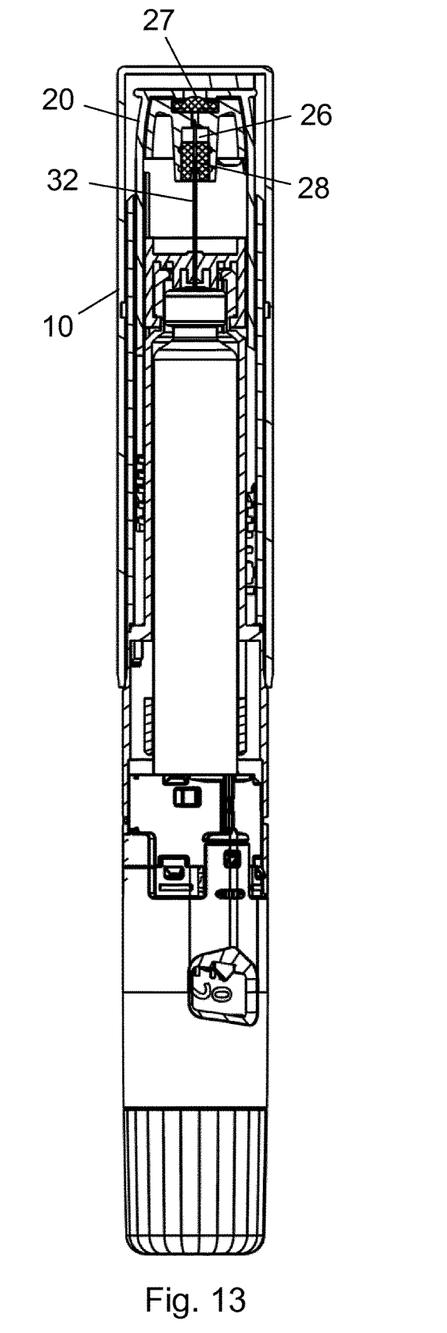
FIG. 13 show a cross sectional view of the injection device during filling of the cleaning chamber.

As the cleaning chamber 26 is filed, the piston 28 is moved in the proximal direction until it encounters a stop 29 as disclosed in FIG. 13. Since the overpressure inside the cartridge 40 can occasionally be larger than the distance the piston 28 is allowed to move proximally due to the stop 29 it is important to vent the system to equalize the pressure before making the injection as will be explained.

FIG. 13 discloses the situation in which the cleaning chamber 26 has been filled as the protective cap 10 has been moved proximally the distance "Y". The piston 28 now abuts the stop 29 and the cleaning chamber 26 is thus filled with drug from the cartridge 40. The liquid system comprising the interior of the cartridge 40, the lumen of the needle cannula 32 and the cleaning chamber 28 can is this situation have an overpressure which can potentially result in overdosing why it is necessary to vent the liquid system.

In the situation disclosed in FIG. 13, the outwardly pointing protrusion 35 is located in the distal end of the axial track 24 as disclosed in FIG. 7.

The user then starts to rotate the protective cap 10 as indicated by the arrow "R" in FIG. 2. This courses the telescopically movable shield 20 also to rotate and to move in the proximal direction due to engagement between the helical track 28 and the outwardly pointing protrusion 35.

Figure 14:
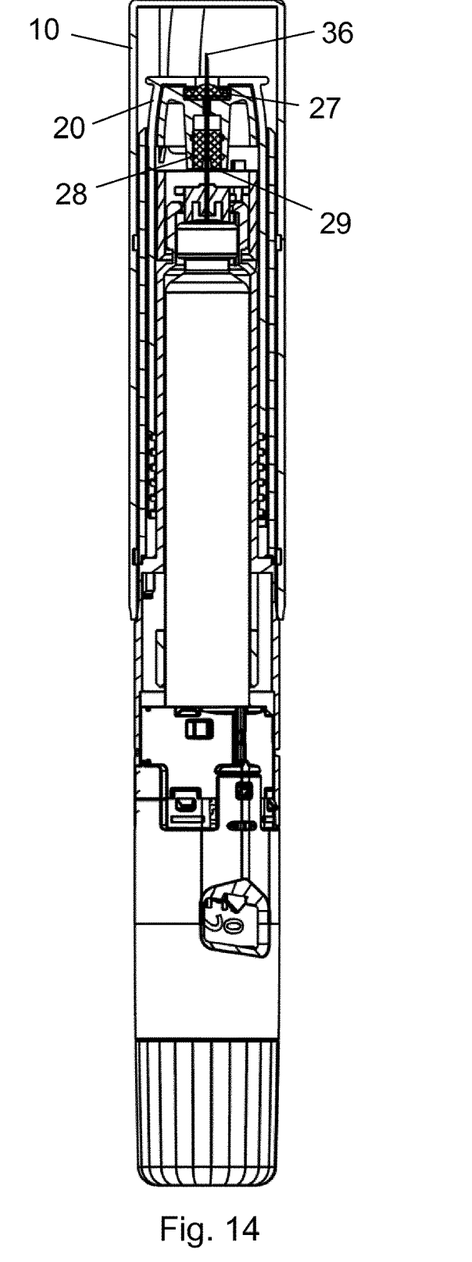
FIG. 14 show a cross sectional view of the injection device with the protective cap rotated to the position of FIG. 3 and FIG. 8.
Figure 15:
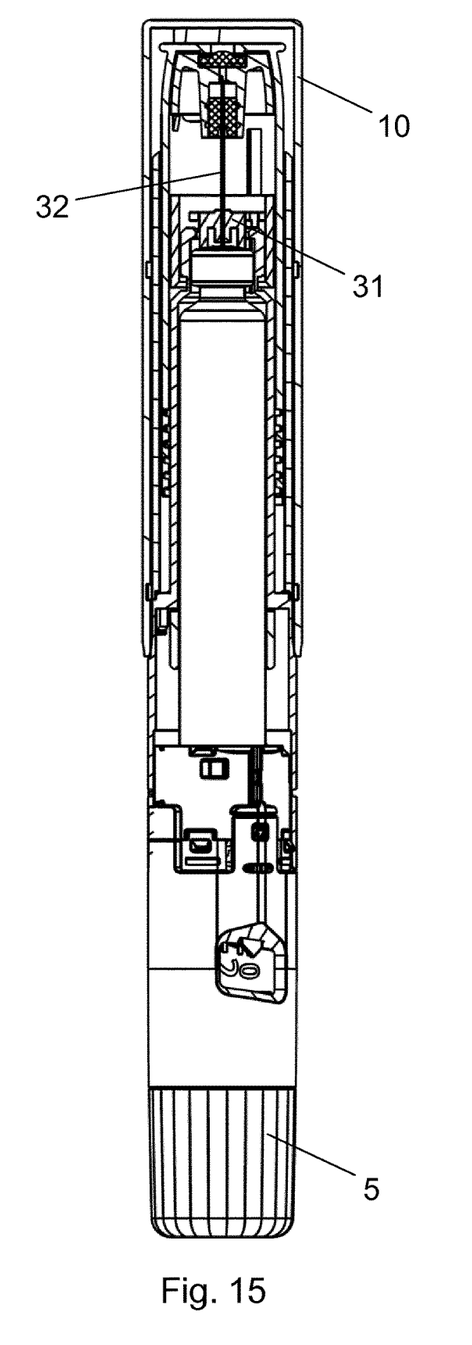
FIG. 15 show a cross sectional view of the injection device in a ready-to-use situation with the protective cap mounted.

As the telescopically movable shield 20 is rotated it move helically in the proximal direction and the sharp tip 36 of the needle cannula 32 penetrates through the distal septum 27 as depicted in FIG. 14. In this position, the overpressure will be equalized by a small quantum of drug automatically being ejected into the interior of the protective cap 10.

In order to collect the ejected amount of liquid drug, the protective cap 10 can internally be provided with a small absorbent sponge or the like.

In FIG. 3, the user keeps rotating the protective cap 10 and thus the telescopically movable shield 20 until the outwardly protrusion 35 enters the second axial track 25 as depicted in FIG. 8. The situation disclosed in FIG. 8 where the outwardly pointing protrusion 35 abuts the sidewall of the second axial track 25 equals the situation in FIG. 14 wherein the distal tip 36 of the needle cannula 32 protrudes beyond the distal septum 27 thus venting the liquid system. However, in this situation, the non-shown spring urges the telescopically movable shield 20 in the distal direction as indicated by the arrow "A" in FIG. 9 such that the distal tip 36 of the needle cannula 32 is positioned inside the cleaning chamber 26 as disclosed in FIG. 15. In this situation the injection device 1 is ready for use.

Since the overpressure has now been equalized, the dose injected is identical to the dose set by the user using the dose setting button 5.

Figure 16:
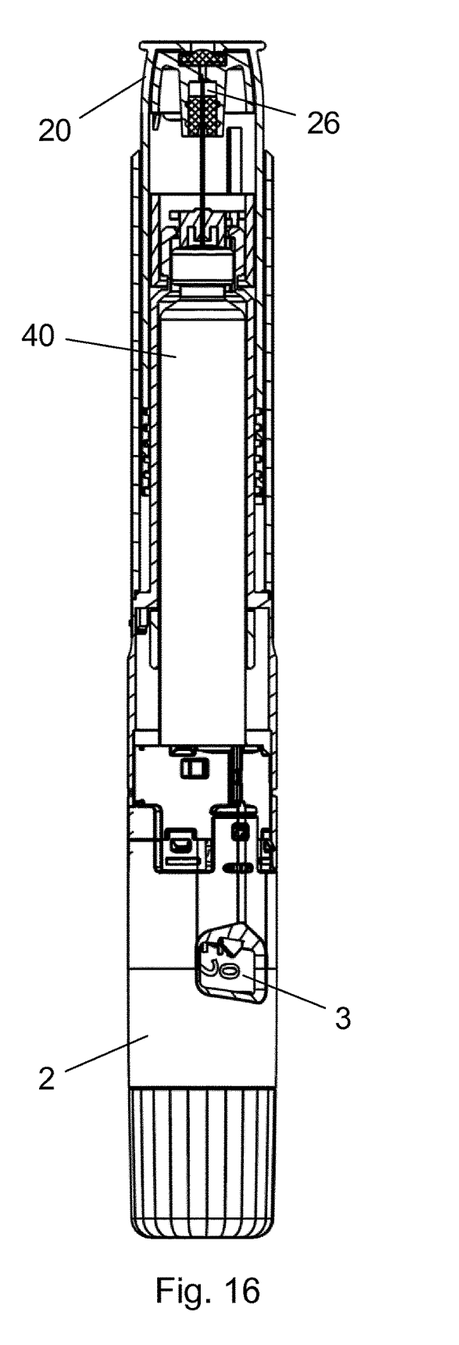
FIG. 16 show a cross sectional view of the injection device in a ready-to-use situation with the protective cap removed.

In the ready-to-use situation, the user only needs to set the required dose and remove the protective cap 20 as disclosed in FIG. 16. The telescopically movable shield 20 is now slidable in the length of the second axial track 25 and the telescopically movable shield 20 can slide between the two positions of the outwardly pointing protrusion 35 disclosed in FIG. 9 and FIG. 10 as indicted by the arrow "B" in FIG. 10.

Figures 9, 10:
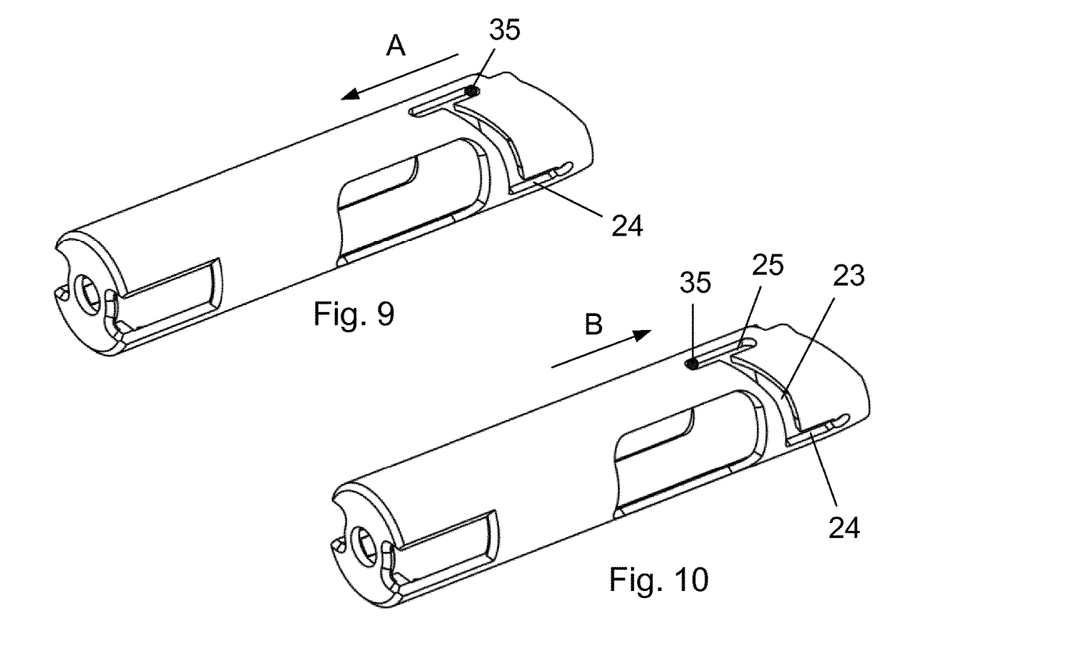

When the shield 20 is positioned in the position disclosed in FIG. 10, the distal tip 36 of the needle cannula 32 has penetrated through the skin of the user and the set dose is released. Usually the injection device 1 would be an automatic torsion spring operated injection device wherein the torque stored in the torsion spring would be released by the proximal movement of the shield 20.

Some preferred embodiments have been shown in the foregoing, but it should be stressed that the invention is not limited to these, but may be embodied in other ways within the subject matter defined in the following claims.

The invention claimed is:

1. A pre-filled injection device for apportioning set doses of a liquid drug comprising:
   A pen-shaped housing extending in a longitudinal direction and having a needle supporting distal end,
   A removable protective cap mountable on the housing and covering at least a part of the needle supporting distal end between injections, and which removable protective cap is rotatable relatively to the housing when mounted there upon,
   A non-replaceable cartridge permanently embedded in the housing of the pre-filled injection device and having an interior containing the liquid drug,
   A needle assembly comprising a needle cannula secured in a hub which needle cannula has a distal end with a distal tip and a proximal end and wherein the proximal end of the needle cannula is inserted into the cartridge,
   A telescopically movable shield movable from an extended position covering at least the distal tip of the needle cannula to a retracted position and which telescopically movable shield carries a cleaning chamber containing an amount of the same liquid drug as contained in the cartridge for cleaning at least the distal tip of the needle cannula between subsequent injections, and which telescopically movable shield is rotatably mounted relatively to the housing, wherein
   the removable protective cap when mounted engages the telescopically movable shield such that rotation of the protective cap relatively to the housing is transformed to a rotation of the telescopically movable shield.

2. A pre-filled injection device according to claim 1, wherein the protective cap internally is provided with the structure for engaging the shield.

3. A pre-filled injection device according to claim 2, wherein the structure provided internally in the protective cap is a gripping structure for engaging a longitudinal track provided in the shield.

4. A pre-filled injection device according to claim 3, wherein the gripping structure is formed with shoulders for transferring an axial force on to the telescopically movable shield.

5. A pre-filled injection device according to claim 1, wherein the telescopically movable shield is provided with a guiding track.

6. A pre-filled injection device according to claim 5, wherein the injection device is provided with a protrusion engaging the guiding track.

7. A pre-filled injection device according to claim 6, wherein the protrusion is provided on the housing or on a part of the housing.

8. A pre-filled injection device according to claim 5, wherein the guiding track has a helical track part.

9. A pre-filled injection device according to claim 8, wherein the helical track part connects a first axial track part and a second axial track part.

10. A pre-filled injection device according to claim 1, wherein the telescopically movable shield is urged distally by resilient spring structure.

11. A pre-filled injection device according to claim 1, wherein the needle assembly is slidable mounted relatively to the housing.

* * * * *